US011241200B2

(12) United States Patent
Oishi et al.

(10) Patent No.: US 11,241,200 B2
(45) Date of Patent: Feb. 8, 2022

(54) X-RAY COMPUTED TOMOGRAPHY APPARATUS

(71) Applicants: TOSHIBA MEDICAL SYSTEMS CORPORATION, Otawara (JP); KEIO UNIVERSITY, Minato-ku (JP)

(72) Inventors: Keisuke Oishi, Nasushiobara (JP); Katsumi Gotanda, Nasushiobara (JP); Masahiro Jinzaki, Tokyo (JP); Takeo Nagura, Tokyo (JP); Naomichi Ogihara, Yokohama (JP)

(73) Assignees: CANON MEDICAL SYSTEMS CORPORATION, Otawara (JP); KEIO UNIVERSITY, Minato-ku (JP)

( * ) Notice: Subject to any disclaimer, the term of this patent is extended or adjusted under 35 U.S.C. 154(b) by 46 days.

(21) Appl. No.: 15/711,650

(22) Filed: Sep. 21, 2017

(65) Prior Publication Data
US 2018/0008210 A1    Jan. 11, 2018

(30) Foreign Application Priority Data

Sep. 26, 2016  (JP) .............................. JP2016-187550
Sep. 15, 2017  (JP) .............................. JP2017-177697

(51) Int. Cl.
*A61B 6/04* (2006.01)
*A61B 6/00* (2006.01)
*A61B 6/03* (2006.01)

(52) U.S. Cl.
CPC ............... *A61B 6/04* (2013.01); *A61B 6/032* (2013.01); *A61B 6/4435* (2013.01)

(58) Field of Classification Search
CPC .......... A61B 6/04; A61B 6/032; A61B 6/4435
See application file for complete search history.

(56) References Cited

U.S. PATENT DOCUMENTS 3,700,894 A * 10/1972 Counsell ................. A61B 6/04
                                                              378/205
4,044,265 A *  8/1977 Schmidt ............... A61B 6/0478
                                                              378/39

(Continued)

FOREIGN PATENT DOCUMENTS

JP    H02-123211 U    10/1990
JP    H06-98885 A      4/1994

(Continued)

OTHER PUBLICATIONS

Japanese Office Action dated Jul. 6, 2021, issued in Japanese Patent Application No. 2017-177697.

*Primary Examiner* — David P Porta
*Assistant Examiner* — Shun Lee
(74) *Attorney, Agent, or Firm* — Oblon, McClelland, Maier & Neustadt, L.L.P.

(57) ABSTRACT

According to one embodiment, an X-ray computed tomography apparatus includes a gantry body, a column, and fixing equipment. The gantry body includes a bore to form a field of view, and also includes an X-ray tube and an X-ray detector. The column supports the gantry body so that the gantry body is vertically movable with a central axis of the bore extending vertically to a floor face. The fixing equipment fixes a subject holder so that the subject holder is located on a passage of the bore and partially in the bore in a phase of attaching a subject to the subject holder.

14 Claims, 8 Drawing Sheets

(56) References Cited

U.S. PATENT DOCUMENTS

| | | |
|---|---|---|
| 2008/0209085 A1 | 8/2008 | Fukawa |
| 2011/0176717 A1* | 7/2011 | Siren .................. A61B 6/06 382/131 |
| 2014/0139215 A1* | 5/2014 | Gregerson ............... A61B 6/04 324/309 |

FOREIGN PATENT DOCUMENTS

| | | |
|---|---|---|
| JP | 3140438 U | 3/2008 |
| JP | 2008-210280 | 9/2008 |
| JP | 2013-9819 | 1/2013 |
| JP | 2014-12055 | 1/2014 |

* cited by examiner

X-RAY COMPUTED TOMOGRAPHY APPARATUS

CROSS-REFERENCE TO RELATED APPLICATIONS

This application is based upon and claims the benefit of priority from Japanese Patent Application No. 2016-187550, filed Sep. 26, 2016, and Japanese Patent Application No. 2017-177697, filed Sep. 15, 2017, the entire contents of all of which are incorporated herein by reference.

FIELD

Embodiments described herein relate generally to an X-ray computed tomography apparatus.

BACKGROUND

X-ray computed tomography is usually performed on a patient who is in the lying position on a bed. However, when X-ray computed tomography is used to diagnose deglutition disorders and the like, it is desirable that a patient be in the standing position. X-ray computed tomography for patients in the standing position has not yet been put to practical use.

DETAILED DESCRIPTION

According to one embodiment, an X-ray computed tomography apparatus includes a gantry body, a column, and fixing equipment. The gantry body includes a bore to include a field of view, and also includes an X-ray tube and an X-ray detector. The column supports the gantry body so that the gantry body is vertically movable with a central axis of the bore extending vertically to a floor face. The fixing equipment fixes a subject holder so that the subject holder is located on a passage of the bore and partially in the bore in a phase of attaching a subject to the subject holder.

The X-ray computed tomography apparatus according to this embodiment will now be described with reference to the accompanying drawings.

Figure 1:
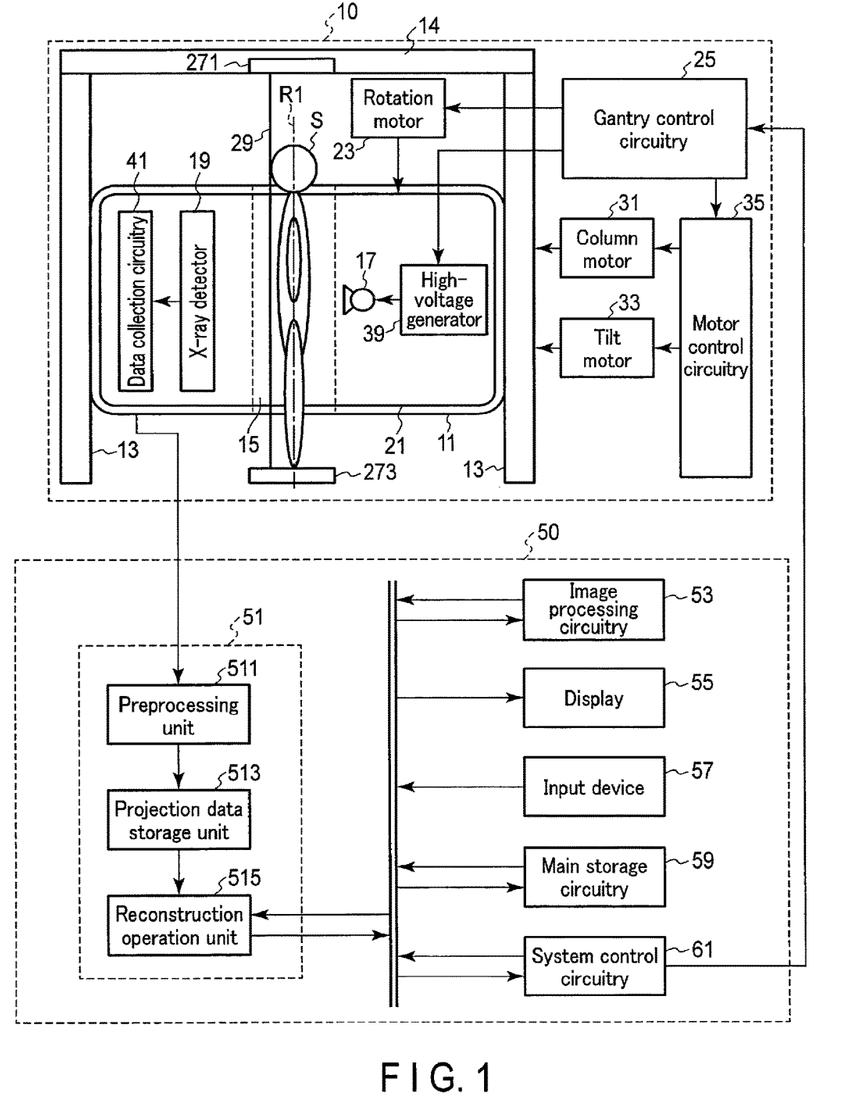
FIG. 1 shows a configuration of an X-ray computed tomography apparatus according to one embodiment.

FIG. 1 shows a configuration of the X-ray computed tomography apparatus according to the embodiment. As shown in FIG. 1, this X-ray computed tomography apparatus includes a gantry 10 and a console 50. For example, the gantry 10 is installed in a CT examination room and the console 50 is installed in a control room adjacent to the CT examination room. The gantry 10 and the console 50 are communicably connected to each other by wire or wirelessly. The gantry 10 is a scanner that is configured for X-ray computed tomography (hereinafter, "X-ray CT") for a standing subject S. The console 50 is a computer that controls the gantry 10.

Figure 2:
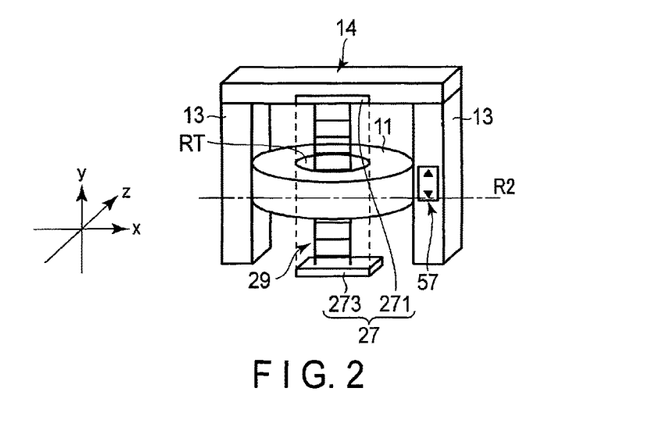
FIG. 2 is an external view of the gantry of FIG. 1.

The gantry 10 includes a gantry body 11, a column 13, and a beam 14. FIG. 2 is an external view of the gantry 10. For the succeeding descriptions, the direction vertical to a floor face is assumed to be a Y direction, the direction parallel to a horizontal axis R2 that is horizontally orthogonal to a central axis R1 of a bore 15 is assumed to be an X direction, and the direction orthogonal to the Y and X directions is assumed to be a Z direction.

As shown in FIG. 2, the gantry body 11 is a substantially cylindrical structure having the bore 15 to form a field of view. As shown in FIG. 1, the gantry body 11 includes an X-ray tube 17 and an X-ray detector 19 which are opposed to each other with the bore 15 therebetween.

In greater detail, the gantry body 11 further includes a main frame (not shown) formed of a metal such as aluminum, and a rotation frame 21 rotatably supported by the main frame around the central axis R1 using bearings, etc. A slip ring (not shown) is provided at a portion of the main frame that contacts the rotation frame 21. A conductive brush (not shown) is attached to this contact portion of the main frame for sliding contact with the slip ring. The rotation frame 21 is an annular metal frame of aluminum, etc. and has components such as the X-ray tube 17 and the X-ray detector 19 attached thereto. For example, the X-ray tube 17 and the X-ray detector 19 may be fitted to a concave portion formed in the rotation frame 21, or they may be fastened to the rotation frame 21 using fastening elements such as screws.

The rotation frame 21 rotates about the central axis R1 at a constant angular velocity by receiving power from a rotation motor 23. The rotation motor 23 causes power to rotate the rotation frame 21 under the control of gantry control circuitry 25. The rotation motor 23 generates the power by driving at a rotational rate corresponding to, for example, a duty ratio of drive signals from the gantry control circuitry 25. The rotation motor 23 may be realized by a direct drive motor, a servo motor, etc. The rotation motor 23 is disposed in, for example, the gantry body 11.

As shown in FIG. 2, the column 13 serves as a base for supporting the gantry body 11 away from the floor face. Specifically, the column 13 supports the gantry body 11 so that the gantry body 11 can slide in the direction perpendicular to the floor face. The column 13 supports the gantry body 11 so that the gantry body 11 can also rotate about the horizontal axis. The column 13 is made of a metal, a reinforced plastic material, or the like. The beam 14 is provided on the column 13, or bridges over a pair of columns 13. The beam 14 is made of a metal, a reinforced plastic material, or the like. The beam 14 is typically of the same material as the column 13. The column 13 and the beam 14 may be integral.

Typically, two columns 13 are provided as a pair. Along the X direction, one column 13 is connected to one side of the gantry body 11 and the other column 13 is connected to the other side of the gantry body 11. However, this is not a limitation to the embodiment. For example, the embodiment may adopt one column 13 connected to only one side of the gantry body 11. Also, while a pillar shape can be supposed for the column 13, this is not a limitation to the embodiment. The column 13 may have any shape including a U-shape, etc., provided that it is capable of supporting the gantry body 11 via at least one side thereof.

The column 13 need not immobilize the gantry body 11 in a state that the central axis R1 is extending along the vertical Y direction. In other words, the column 13 may be configured to support the gantry body 11 so that the gantry body 11 is rotatable about the horizontal axis R2. Specifically, the column 13 and the gantry body 11 may be connected via bearings, etc. to allow the gantry body 11 to rotate about the horizontal axis R2. Below, it will be assumed that the column 13 supports the gantry body 11 so that the gantry body 11 can slide in the longitudinal direction and rotate (tilt) about the horizontal axis R2. Thanks to the column 13 configured to support the gantry body 11 around the horizontal axis R2, one gantry 10 can suffice for the X-ray CT for a standing subject as shown in FIG. 1, as well as for the X-ray CT for a lying subject.

The column 13 can support the gantry body 11 in a posture to maintain the central axis R1 extending in the Y direction or in the Z direction. Not only this, the column 13 may also keep the gantry body 11 stationary with the central axis R1 oriented at any angle with respect to the horizontal axis R2.

Holder fixing equipment 27 is provided for fixing a subject holder 29 in a passage RT along which the bore 15 is moved. The subject holder 29 is a device for retaining a subject within the passage RT of the bore 15. Specifically, the holder fixing equipment 27 fixes the subject holder 29 in the passage RT of the bore 15 when the gantry body 11 is arranged with the central axis of the bore 15 extending perpendicularly to the floor face.

The holder fixing equipment 27 includes an upper fixing part 271 and a lower fixing part 273. The upper fixing part 271 is provided at a portion of the beam 14. The upper fixing part 271 is located at the position of the beam 14 that intersects with the passage RT. The upper fixing part 271 may take in the subject holder 29. For example, the upper fixing part 271 can include the subject holder 29 in such a manner that it reels and accommodates the subject holder 29. The subject holder 29 adapted to reeling would be, for example, a rope-like elastic or semi-rigid member. In this case, the subject holder 29 is built from carbon, wood, vinyl materials, etc., for example. The upper fixing part 271 discharges the subject holder 29 to insert it into the bore 15, and reels it to take out from the bore 15.

The subject holder 29 may also be built from, for example, multiple ladder-like rigid members (ladder members) that can slide in the Y direction. In other words, the subject holder 29 includes multiple ladder members which are mutually coupled in a nested structure. The subject holder 29 can freely elongate and contract by sliding the multiple ladder members. In this case, the upper fixing part 271 deploys the subject holder 29 to insert it into the bore 15, and folds it to take it out from the bore 15.

Preferably, the subject holder 29 should adopt materials that do not contain high X-ray absorbent components, such as metals, in order to prevent noise in CT images. In other words, the subject holder 29 may be formed of non-metal materials.

The lower fixing part 273 is located at the position of the floor face that intersects with the passage of the bore 15, and fixes the bottom portion of the subject holder 29. The lower fixing part 273 catches the subject holder 29 that can be inserted into and taken out from the bore 15. The lower fixing part 273 is, for a specific example, a rigid device having a hook shape. After the subject holder 29 is hooked by the lower fixing part 273, the upper fixing part 271 reels and tensions the subject holder 29. The lower fixing part 273 may also specifically be, for example, a magnet that by itself attracts the approaching subject holder 29 having a magnet at the lower end. Note that the upper fixing part 271 and the lower fixing part 273 may be replaced with each other. In that case, the lower fixing part 273 is located at the position intersecting with the passage RT and includes the subject holder 29.

As shown in FIG. 1, the column 13 includes a column motor 31 for sliding the gantry body 11 in the Y direction and a tilt motor 33 for tilting the gantry body 11. The column motor 31 causes power to slide the gantry body 11 in the longitudinal direction under the control of motor control circuitry 35. Specifically, the column motor 31 generates the power by driving at a rotational rate corresponding to, for example, a duty ratio of drive signals from the motor control circuitry 35. The column 13 slides the gantry body 11 in the longitudinal direction of the column 13 by receiving the power from the column motor 31. The tilt motor 33 causes power to rotate the gantry body 11 about the horizontal axis R2 under the control of the motor control circuitry 35. Specifically, the tilt motor 33 generates the power by driving at a rotational rate corresponding to, for example, a duty ratio of drive signals from the motor control circuitry 35. The column 13 rotates the gantry body 11 about the horizontal axis R2 by receiving the power from the tilt motor 33. The column motor 31 and the tilt motor 33 may be realized by a motor such as a servo motor.

The motor control circuitry 35 controls the column motor 31 and the tilt motor 33 under the control of the gantry control circuitry 25. For example, the motor control circuitry 35 controls the column motor 31 to raise and lower the gantry body 11 from the maximum height to the minimum height in a given range. The motor control circuitry 35 includes a processor and a memory as hardware resources. Examples of the processor include a central processing unit (CPU) and a micro processing unit (MPU), and examples of the memory include a read only memory (ROM) and a random access memory (RAM). The motor control circuitry 35 may also be realized by an application specific integrated circuit (ASIC) or a field programmable gate array (FPGA), or other complex programmable logic device (CPLD) or a simple programmable logic device (SPLD). The processor reads and executes programs stored in the memory to realize the aforementioned functions. The programs may be incorporated directly in a circuit of the processor, instead of being stored in the memory. In this case, the processor reads the programs incorporated in its circuit and executes them to realize the functions.

As shown in FIG. 1, the X-ray tube 17 receives a high voltage from a high-voltage generator 39 to generate X-rays. The high-voltage generator 39 is attached to, for example, the rotation frame 21. The high-voltage generator 39 generates high voltages for application to the X-ray tube 17 under the control of the gantry control circuitry 25, from the power supplied from a power unit (not shown) of the gantry body 11 via the slip ring. The high-voltage generator 39 and the X-ray tube 17 are connected to each other via a high-voltage cable (not shown). The high voltages generated by the high-voltage generator 39 are applied to the X-ray tube 17 via the high-voltage cable.

The X-ray detector 19 detects X-rays generated by the X-ray tube 17 and transmitted through the subject S. The X-ray detector 19 is provided with a plurality of X-ray detection elements (not shown) arranged on a two-dimensionally curved surface. Each of the X-ray detection elements detects the X-ray from the X-ray tube 17 and converts the detected X-ray into an electrical signal having a wave height value corresponding to the intensity of the X-ray. Each of the X-ray detection elements includes, for example, a scintillator and a photoelectric converter. The scintillator receives an X-ray to generate fluorescence. The photoelectric converter converts the generated fluorescence into a charge pulse. The charge pulse has a wave height value corresponding to the intensity of the x-ray. As the photoelectric converter, a device that converts photons into electrical signals, such as a photomultiplier and a photodiode, is used. The X-ray detector 19 according to this embodiment is not limited to an indirect-detection type detector that first converts an X-ray into fluorescence and then into an electrical signal, but may be a direct-detection type detector that converts an X-ray directly into an electrical signal.

Data collection circuitry 41 collects, for each view, digital data indicative of the intensity of the X-ray attenuated by the subject S. The data collection circuitry 41 is realized by, for example, a semiconductor integrated circuit in which an integration circuit and an A/D converter are arranged in parallel for each of the X-ray detection elements. The data collection circuitry 41 is connected to the X-ray detector 19 within the gantry body 11. The integration circuit integrates the electrical signals from the X-ray detection element for a given view period and generates an integrated signal. The A/D converter converts the generated integrated signal into digital data having a data value corresponding to the wave height value of the integrated signal. This digital data after the conversion is called raw data. The raw data is a set of digital values of the X-ray intensity identified by the channel number and the row number of the originating X-ray detection element and the view number indicative of the data collection subject view. The raw data is sent to the console 50 via, for example, a non-contact data transmitter (not shown) included in the gantry body 11.

The gantry body 11 may include not only the X-ray tube 17, the X-ray detector 19, the rotation frame 21, the main frame, the power unit, the high-voltage generator 39, and the data collection circuitry 41, but also other various devices necessary for CT. For example, a cooler for cooling the X-ray tube may be attached to the rotation frame 21. Also, an air conditioning fan may be furnished on the gantry body 11.

The gantry control circuitry 25 controls the high-voltage generator 39, the rotation motor 23, and the motor control circuitry 35 under the control of system control circuitry 61 of the console 50. The gantry control circuitry 25 includes, as hardware resources, a processor such as CPU, MPU, etc., and a memory such as ROM, RAM, etc. The gantry control circuitry 25 may also be realized by ASIC or FPGA, or CPLD, SPLD, etc. The processor reads and executes programs stored in the memory to realize the above functions. The programs may be incorporated directly in a circuit of the processor, instead of being stored in the memory. In this case, the processor reads the programs incorporated in its circuit and executes them to realize the functions.

The motor control circuitry 35 and the gantry control circuitry 25 may be mounted on separate substrates or a single substrate. The motor control circuitry 35 and the gantry control circuitry 25 may be provided at the column 13 of the gantry body 11 or at the console 50. The closer the motor control circuitry 35 to the column motor 31 and the tilt motor 33, the lower the noise due to the motor control circuitry 35; thus, in order to reduce the noise, the motor control circuitry 35 should preferably be disposed in the column 13. However, disposing the motor control circuitry 35 in the column 13 can increase the volume of the column 13. To prevent the column 13 from increasing in volume, therefore, the motor control circuitry 35 may be disposed in a device other than the column 13, such as the console 50 or a dedicated device. The motor control circuitry 35 and the gantry control circuitry 25 need not be provided in a single device, but may be provided in different devices.

As shown in FIG. 1, the console 50 includes image reconstruction circuitry 51, image processing circuitry 53, a display 55, an input device 57, main storage circuitry 59, and the system control circuitry 61, which are connected via a bus. Data communications between the image reconstruction circuitry 51, the image processing circuitry 53, the display 55, the input device 57, the main storage circuitry 59, and the system control circuitry 61 are performed via the bus.

The image reconstruction circuitry 51 reconstructs a CT image of the subject S based on the raw data from the console 50. Specifically, the image reconstruction circuitry 51 includes a preprocessing unit 511, a projection data storage unit 513, and a reconstruction operation unit 515. The preprocessing unit 511 performs preprocessing on the raw data from the console 50. The preprocessing includes logarithmic conversion and various corrections such as X-ray intensity corrections and offset corrections. The preprocessed raw data is called projection data. The projection data storage unit 513 is a storage device such as an HDD, SSD, and an integrated circuit storage device, provided for storing the projection data generated by the preprocessing unit 511. Based on the projection data, the reconstruction operation unit 515 generates CT images representing the spatial distribution of CT values for the subject S. As an algorithm for the image reconstruction, currently available image reconstruction algorithms would suffice, such as an analytic image reconstruction method including a filtered back projection (FBP) method, a convolution back projection (CBP) method, etc., and a statistic image reconstruction method including a maximum likelihood expectation maximization (ML-EM) method, an ordered subset expectation maximization (OS-EM) method, etc.

The image reconstruction circuitry 51 includes, as hardware resources, a processor such as a CPU, MPU, graphics processing unit (GPU), etc. and a memory such as ROM, RAM, etc. The image reconstruction circuitry 51 may also be realized by ASIC or FPGA, or CPLD, SPLD, etc. The processor reads and executes programs stored in the memory to realize the functions of the preprocessing unit 511 and the reconstruction operation unit 515. The programs may be incorporated directly in a circuit of the processor, instead of being stored in the memory. In this case, the processor reads the programs incorporated in its circuit and executes the functions of the preprocessing unit 511 and the reconstruction operation unit 515. Also, a dedicated hardware circuit serving as the preprocessing unit 511 and a dedicated hardware circuit serving as the reconstruction operation unit 515 may be implemented in the image reconstruction circuitry 51.

The image processing circuitry 53 performs various image processing on the CT image reconstructed by the image reconstruction circuitry 51. For example, if the CT image is volume data, the image processing circuitry 53 performs three-dimensional image processing, such as volume rendering, surface volume rendering, pixel value projection processing, multi-planar reconstruction (MPR) processing, and curved MPR (CPR) processing, on the CT image to produce a display image. The image processing circuitry 53 includes, as hardware resources, a processor such as a CPU, MPU, GPU, etc. and a memory such as ROM, RAM, etc. The image processing circuitry 53 may also be realized by ASIC or FPGA, or CPLD, SPLD, etc.

The display 55 displays various information including two-dimensional CT images and the display images. As the display 55, for example, a CRT display, a liquid crystal display, an organic EL display, an LED display, a plasma display, or any other display known in this technical field may be adopted as appropriate.

The input device 57 receives various instructions and information inputs from a user. As the input device 57, a keyboard, a mouse, and various switches may be adopted. The input device 57 may be provided at the console 50 or the gantry 10. From the viewpoint of patients' and operators' safety, the input device 57 should desirably be provided at the console 50.

The main storage circuitry 59 is a storage device, such as an HDD, SSD, and an integrated circuit storage device, for storing various information. The main storage circuitry 59 may also be a drive device that reads and writes various information from and to a portable storage medium such as a CD-ROM drive, a DVD drive, and a flash memory. For example, the main storage circuitry 59 stores control programs for the CT in this embodiment.

The system control circuitry 61 includes the processor and the memory as discussed above, as hardware resources. The system control circuitry 61 functions as a center of the X-ray computed tomography apparatus according to the embodiment. Specifically, the system control circuitry 61 reads the control programs stored in the main storage circuitry 59, expands them in the memory, and controls each unit of the X-ray computed tomography apparatus in accordance with the expanded control programs.

The image reconstruction circuitry 51, the image processing circuitry 53, and the system control circuitry 61 may be integrated onto a single substrate within the console 50, or implemented on multiple substrates separately from each other.

The X-ray computed tomography apparatus according to this embodiment will be described below in more detail.

The X-ray computed tomography apparatus according to the embodiment includes the holder fixing equipment 27 that fixes the subject holder 29 for maintaining the subject S upright. In the phase of attaching the subject S to the subject holder 29 (hereinafter, "attachment phase"), the holder fixing equipment 27 fixes the subject holder 29 so that the subject S can be safely attached to the subject holder 29 while being arranged within the passage RT.

Figure 3:
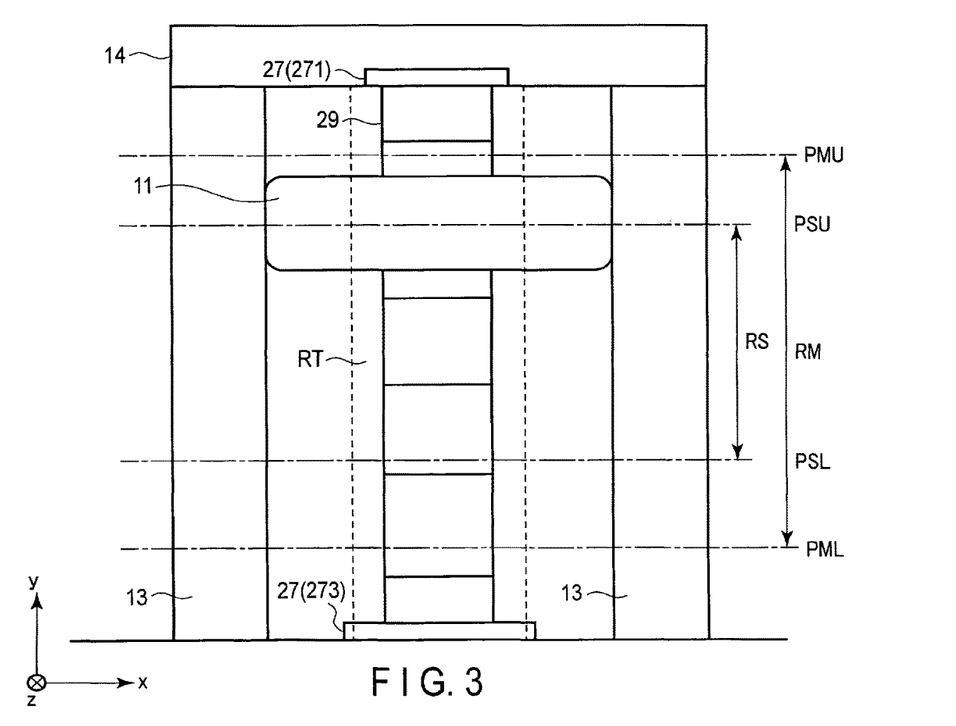
FIG. 3 shows an arrangement of a gantry body and a subject holder in an attachment phase according to the embodiment.

FIG. 3 shows an arrangement of the gantry body 11 and the subject holder 29 in the attachment phase. As shown in FIG. 3, the holder fixing equipment 27 in the attachment phase fixes the subject holder 29 so that the subject holder 29 is partially in the bore 15 and is located in the passage RT of the bore 15.

As shown in FIG. 3, the columns 13 support the gantry body 11 so that the gantry body 11 can ascend and descend in the vertical direction Y. With the columns 13, the gantry body 11 has a mechanical movable range RM that is limited to an upper limit PMU and a lower limit PML by mechanical elements, such as stoppers on the columns 13. For safety, the gantry body 11 during scanning, etc. is electrically limited to a normal movable range RS that is narrower than the mechanical movable range RM. An upper limit PSU of the normal movable range RS is set lower than the upper limit PMU of the mechanical movable range RM, and a lower limit PSL of the normal movable range RS is set higher than the lower limit PML of the mechanical movable range RM.

As shown in FIG. 3, the columns 13 in the attachment phase arrange the gantry body 11 at the upper limit PSU of the normal movable range RS. For example, when an instruction button for the transition to the attachment phase, which may be provided at the column 13, etc., is pressed, the motor control circuitry 35 takes it as a trigger and controls the column motor 31 to place the gantry body 11 at the upper limit PSU. With the gantry body 11 arranged at the upper limit PSU, the subject holder 29 is fixed to the holder fixing equipment 27 so that the subject holder 29 extends through the bore 15 and is contained in the passage RT. By disposing the subject holder 29 in this manner, the subject S can stand directly beneath the gantry body 11 at ease so as to be attached to the subject holder 29.

The holder fixing equipment 27 fixes the longitudinal ends of the subject holder 29 above (+Y direction) and below (−Y direction) the gantry body 11 in the vertical direction. Specifically, the upper longitudinal end of the subject holder 29 is fixed by the upper fixing part 271, and the lower longitudinal end of the subject holder 29 is fixed by the lower fixing part 273. The subject holder 29 can thereby be stabilized. If the subject holder 29 can be made sufficiently stable, the subject holder 29 may be fixed by only one of the upper fixing part 271 and the lower fixing part 273.

The above descriptions have assumed that the gantry body 11 is arranged at the upper limit PSU of the normal movable range RS in the attachment phase. However, the embodiment is not limited to this. For example, the gantry body 11 may be arranged at the upper limit PMU of the mechanical movable range RM in the attachment phase.

Hereinafter, an operation example of the gantry 10 will be described for each mode of fixing the subject holder 29 by the holder fixing equipment 27.

Example 1

Figure 4:
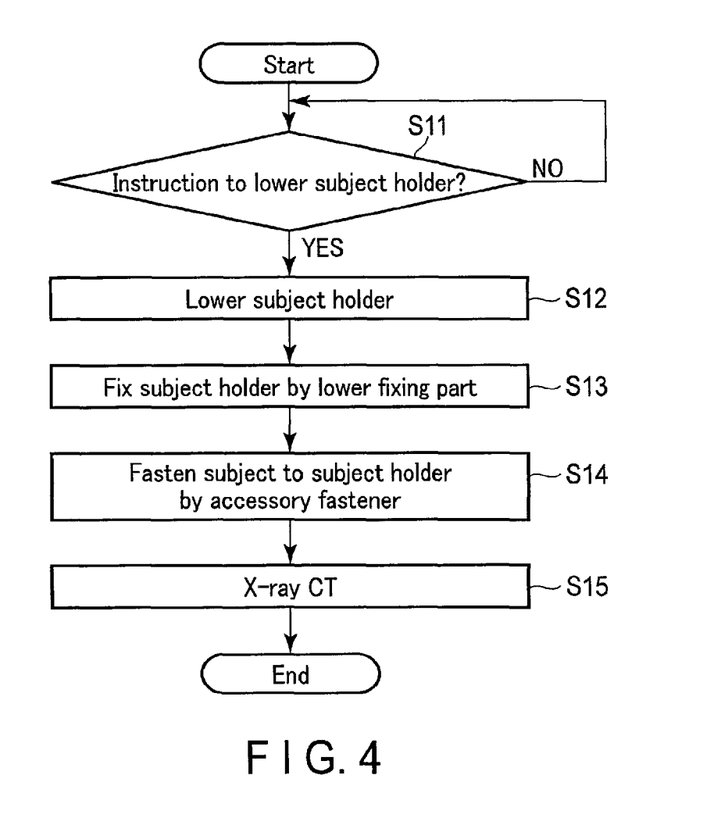
FIG. 4 shows an operation example of an X-ray computed tomography apparatus according to Example 1.

Descriptions will be given of an operation example of the case where the subject holder 29 is included in the upper fixing part 271 and is fixed by the lower fixing part 273. FIG. 4 shows an operation example of the X-ray computed tomography apparatus according to Example 1.

When an instruction to set down the subject holder 29 is input by an operator via the input device 57 (step S11: YES), the system control circuitry 61 or the gantry control circuitry 25 controls the upper fixing part 271 to lower the subject holder 29 (step S12). The subject holder 29 includes a drive mechanism (not shown). The subject holder 29 descends by the driving of the drive mechanism. As described above, the subject holder 29 has a structure adapted to reeling by the drive mechanism. Then, the upper fixing part 271 inserts the subject holder 29 into the bore 15 and takes it out of the bore 15. That is, the upper fixing part 271 discharges and inserts the subject holder 29 into the bore 15, and reels and takes it out of the bore 15. Note that the drive mechanism may be omitted. In that case, the subject holder 29 is allowed to descend by gravity or being manually lowered.

After step S12, the operator fixes the subject holder 29 by the lower fixing part 273 (step S13). In step S13, the operator fixes the subject holder 29 to the floor. Specifically, the lower fixing part 273 includes a hook-shaped device to fix the subject holder 29 to the floor. But the fixing means of the lower fixing part 273 is not limited to this. For example, the lower fixing part 273 may include a magnet. In this case, the lower end of the subject holder 29 is provided with a magnet having a magnetic polarity different from the magnet of the lower fixing part 273. By utilizing the attraction between the magnet of the lower fixing part 273 and the magnet of the subject holder 29, the subject holder 29 is fixed to the floor.

When the subject holder 29 has been fixed by the holder fixing equipment 27 in step S13, followed by the arrangement of the gantry body 11 at the upper limit of the normal movable range or the mechanical movable range, the operation proceeds to the attachment phase. In the attachment phase, as described above, the subject holder 29 is fixed to the holder fixing equipment 27 so that the subject holder 29 extends through the bore 15 and is contained in the passage RT.

Figure 5:
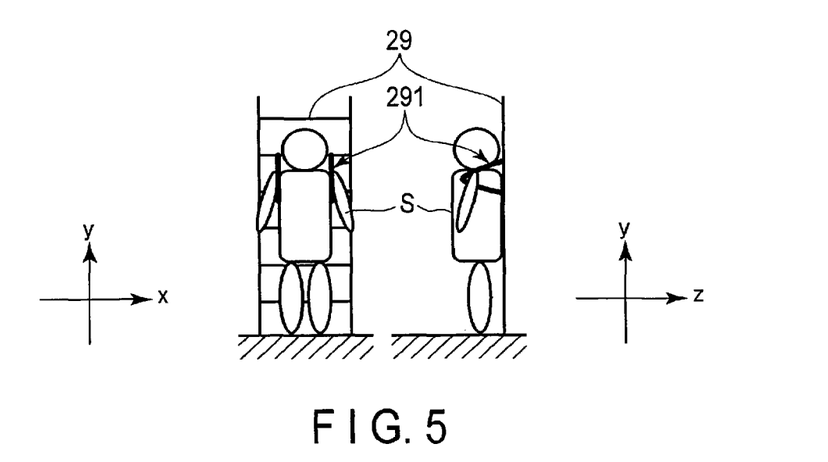
FIG. 5 is a diagram for explaining fastening a subject to a subject holder using fasteners of the subject holder.

After step S13, the operator fastens the subject S to the subject holder 29 using an accessory fastener 291 (step S14). FIG. 5 shows the subject S fastened to the subject holder 29 by the accessory fasteners 291 furnished to the subject holder 29, according to this embodiment. The accessory fastener 291 may, for example, specifically be a belt. With the subject holder 29 and the accessory fastener 291, the subject's posture for the X-ray CT is secured. The holder fixing equipment 27 may support the subject holder 29 movably in the vertical direction Y and the horizontal directions X and Z. Specifically, the holder fixing equipment 27 may be configured to move up, down, right, and left to adjust the position of the subject S held by the subject holder 29 within the passage RT. This enables the positioning of an imaging site with respect to the effective field of view (FOV).

At any timing after step S14, the operator inputs an instruction to start X-ray CT via the input device 57, and the X-ray CT starts (step S15). In step S15, the gantry body 11 is slid from up to down to perform the X-ray CT.

The X-ray computed tomography apparatus according to the embodiment can also be adopted for imaging the subject in the prone or lying position. For example, the gantry body 11 is tilted about the horizontal axis (tilt axis) R2 so that the central axis R1 of the bore 15 extends horizontally. This enables the lying subject S to be positioned in the bore 15 of the gantry body 11 and to undergo prone or lying position imaging. Note that the tilt function is not a requisite for the present embodiment.

As described, the X-ray computed tomography apparatus according to Example 1 can lower the subject holder 29 from the upper fixing part 271. The lowered subject holder 29 can be fixed to the lower fixing part 273. The subject S is held by the subject holder 29 using the accessory fastener 291 so that X-ray CT can be performed for the subject S in the standing position. Since the subject holder 29 is accommodated in the upper fixing part 271, the subject holder 29 does not interfere with the operator or the subject (patient). Also, since the subject holder 29 extends through the bore 15, subjects (patients) are freed from unwanted body motions and their safety and sense of security can be ensured. Therefore, according to Example 1, X-ray computed tomography apparatuses capable of holding and imaging the standing subject S at a given position can be provided.

Example 2

Figure 6:
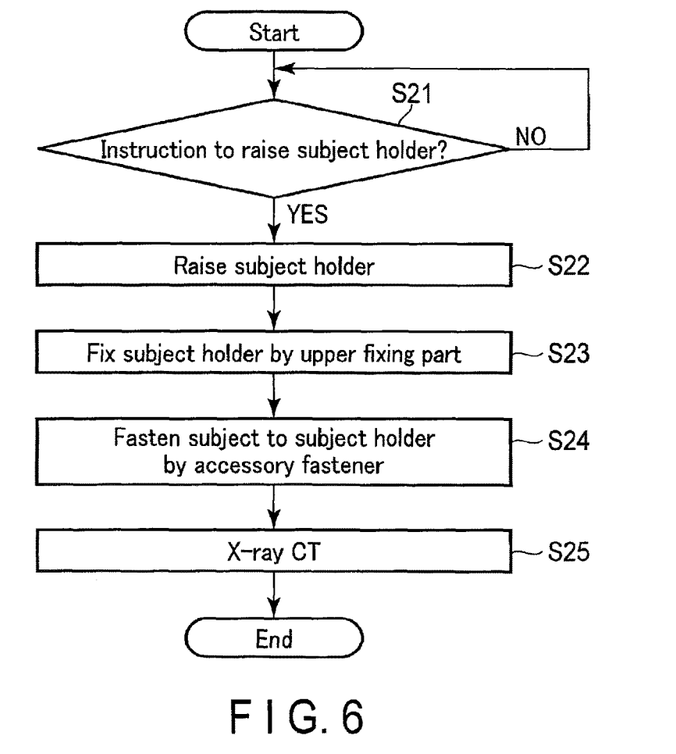
FIG. 6 shows an operation example of an X-ray computed tomography apparatus according to Example 2.

Descriptions will be given of an operation example of the case where the subject holder 29 is included in the lower fixing part 273 and is fixed by the upper fixing part 271. FIG. 6 shows an operation example of the X-ray computed tomography apparatus according to Example 2.

When an instruction to raise the subject holder 29 is input by an operator via the input device 57 (step S21: YES), the system control circuitry 61 controls the lower fixing part 273 to raise the subject holder 29 (step S22). The subject holder 29 includes a drive mechanism (not shown). The subject holder 29 ascends by the driving of the drive mechanism. The drive mechanism may be omitted, and in that case, the subject holder 29 is raised manually.

After step S22, the operator fixes the subject holder 29 by the upper fixing part 271 (step S23). Specifically, the upper fixing part 271 includes a hook-shaped device to fix the subject holder 29 to the beam 14 or a ceiling, but the fixing means of the upper fixing part 271 is not limited to this. For example, the upper fixing part 271 may include a magnet. In this case, the upper end of the subject holder 29 is provided with a magnet having a magnetic polarity different from the magnet of the upper fixing part 271. By utilizing the attraction between the magnet of the upper fixing part 271 and the magnet of the subject holder 29, the subject holder 29 is fixed to the beam 14 or the ceiling.

When the subject holder 29 has been fixed by the holder fixing equipment 27 in step S23, followed by the arrangement of the gantry body 11 at the upper limit of the normal movable range or the mechanical movable range, the operation proceeds to the attachment phase. In the attachment phase, as described above, the subject holder 29 is fixed to the holder fixing equipment 27 so that the subject holder 29 extends through the bore 15 and is contained in the passage RT.

After step S23, the operator fastens the subject S to the subject holder 29 using an accessory fastener (step S24).

At any timing after step S24, the operator inputs an instruction to start X-ray CT via the input device 57, and the X-ray CT starts (step S25). In step S25, the gantry body 11 is slid from down to up to perform the X-ray CT.

As described, the X-ray computed tomography apparatus according to Example 2 can raise the subject holder 29 from the lower fixing part 273. The raised subject holder 29 can be fixed to the upper fixing part 271. The subject S is held by the subject holder 29 using the accessory fastener 291 so that X-ray CT can be performed for the subject S in the standing position. Since the subject holder 29 is accommodated in the lower fixing part 273, the subject holder 29 does not interfere with the operator or the subject (patient). Therefore, according to Example 2, X-ray computed tomography apparatuses capable of holding and imaging the standing subject S at a given position can be provided.

Example 3

Figure 7:
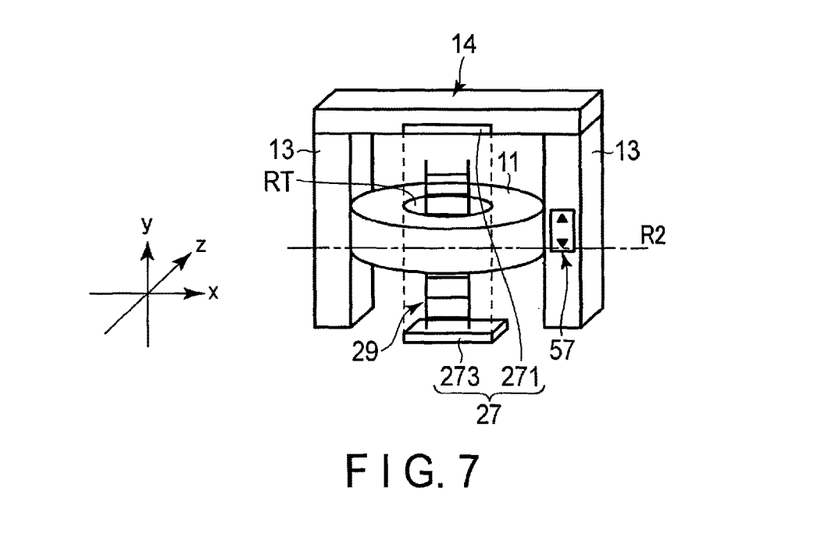
FIG. 7 is an external view of a gantry according to Example 3.

FIG. 7 is an external view of the gantry according to Example 3. The X-ray computed tomography apparatus according to Example 3 fixes the subject holder 29 only by the lower fixing part 273. The lower fixing part 273 is, for example, a recess in the floor that can make the subject holder 29 stand in a given position, or the lower fixing part 273 may be a mark for determining where to place the subject holder 29. The subject holder 29 is, for example, a ladder or a chair.

Figure 8:
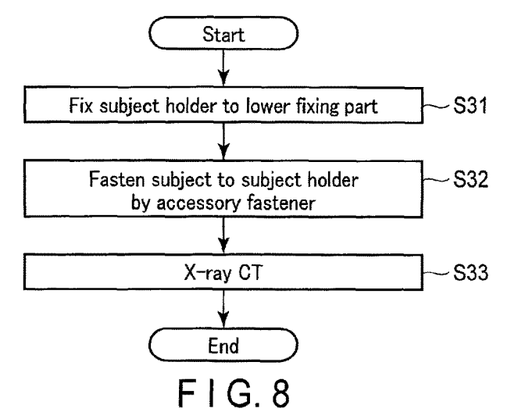
FIG. 8 shows an operation example of an X-ray computed tomography apparatus according to Example 3.

Descriptions will be given of an operation example in the case where the subject holder 29 is fixed by the lower fixing part 271. FIG. 8 shows an operation example of the X-ray computed tomography apparatus according to Example 3.

The operator fixes the subject holder 29 by the lower fixing part 273 (step S31). In step S31, the operator fixes the subject holder 29 by inserting it to the lower fixing part 273 which may concretely be a recessed part.

When the subject holder 29 has been fixed by the holder fixing equipment 27 in step S31, followed by the arrangement of the gantry body 11 at the upper limit of the normal movable range or the mechanical movable range, the operation proceeds to the attachment phase. In the attachment phase, as described above, the subject holder 29 is fixed to the holder fixing equipment 27 so that the subject holder 29 extends through the bore 15 and is contained in the passage RT.

After step S31, the operator fastens the subject S to the subject holder 29 using an accessory fastener (step S32).

At any timing after step S32, the operator inputs an instruction to start X-ray CT via the input device 57, and the X-ray CT starts (step S33).

As described, the X-ray computed tomography apparatus according to Example 3 fixes the subject holder 29 to the lower fixing part 273. The subject S is fastened to the fixed subject holder 29 using the accessory fastener so that X-ray CT can be performed for the upright subject S. Therefore, according to Example 3, X-ray computed tomography apparatuses capable of holding and imaging the upright subject S at a given position can be provided.

Modification Examples

The subject holder 29 is not limited to the structures described above. The subject holder 29 may be a pillar or multiple pillars.

Figure 9:
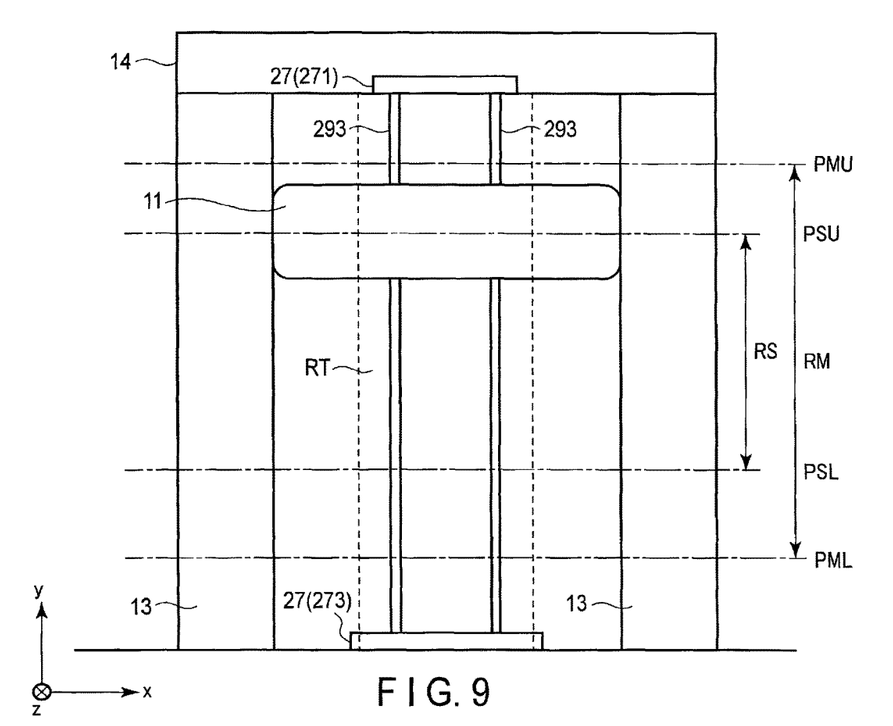
FIG. 9 shows an example of a subject holder including two pillars according to one modification example of the embodiment.
Figure 10:
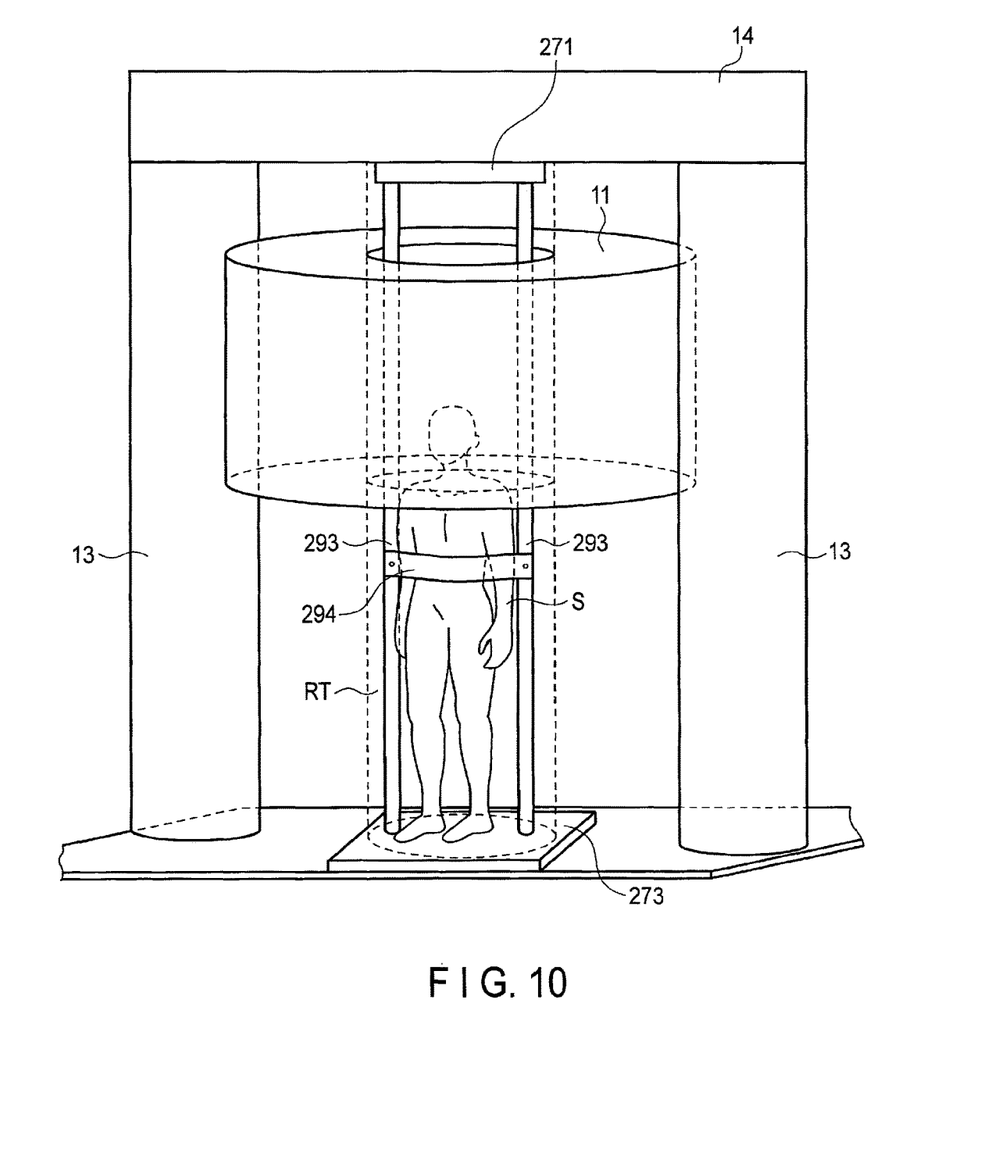
FIG. 10 shows the subject holder of FIG. 9 and a subject.

FIG. 9 shows one example of the subject holder 29 including two pillars 293. FIG. 10 shows the dual-pillar subject holder 293 of FIG. 9 together with a subject S. As shown in FIGS. 9 and 10, the two pillars 293 are fixed by the holder fixing equipment 27. Specifically, the upper ends of the two pillars 293 are fixed by the upper fixing part 271, and the lower ends of the two pillars 293 are fixed by the lower fixing part 273. The two pillars 293 may be provided in any arrangement within the passage RT. For example, the upper fixing part 271 and the lower fixing part 273 fix the two pillars 293 so that the two pillars 293 are located on the respective sides of the subject S as shown in FIGS. 9 and 10.

In order to more reliably secure the subject S to the two pillars 293, an accessory fastener 294, such as a band, may be detachably provided to the two pillars 293 as shown in FIG. 10. With the accessory fastener 294, the subject S can be fastened to the two pillars 293.

Figure 11:
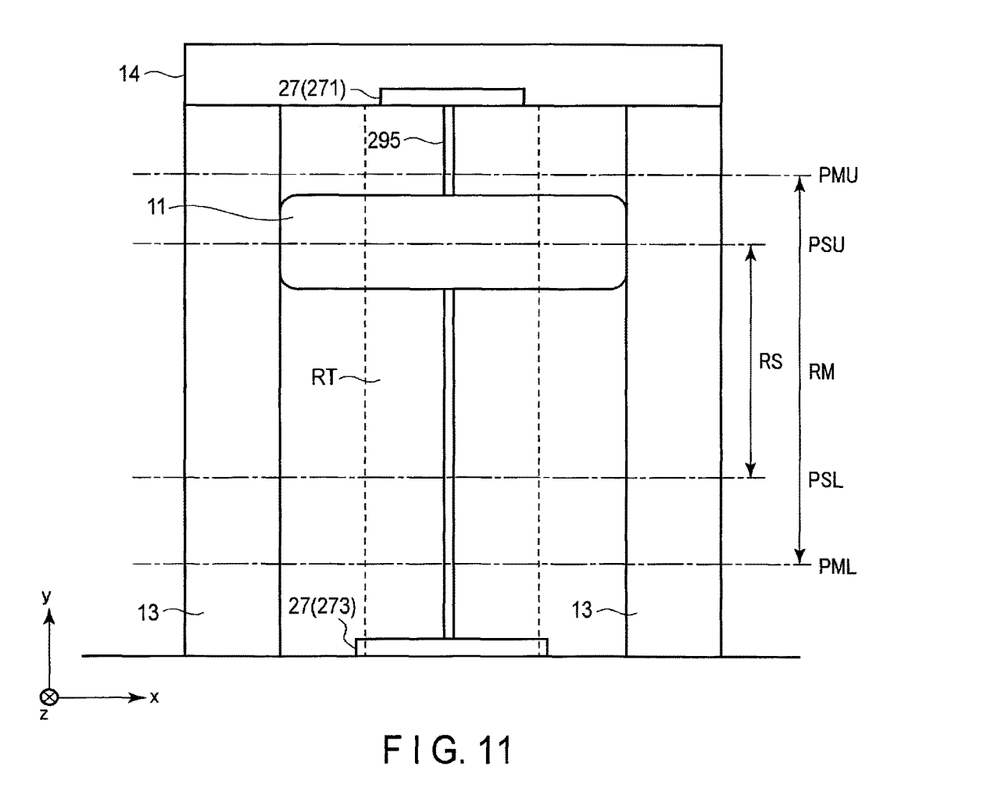
FIG. 11 shows an example of a subject holder including one pillar according to one modification example of the embodiment.
Figure 12:
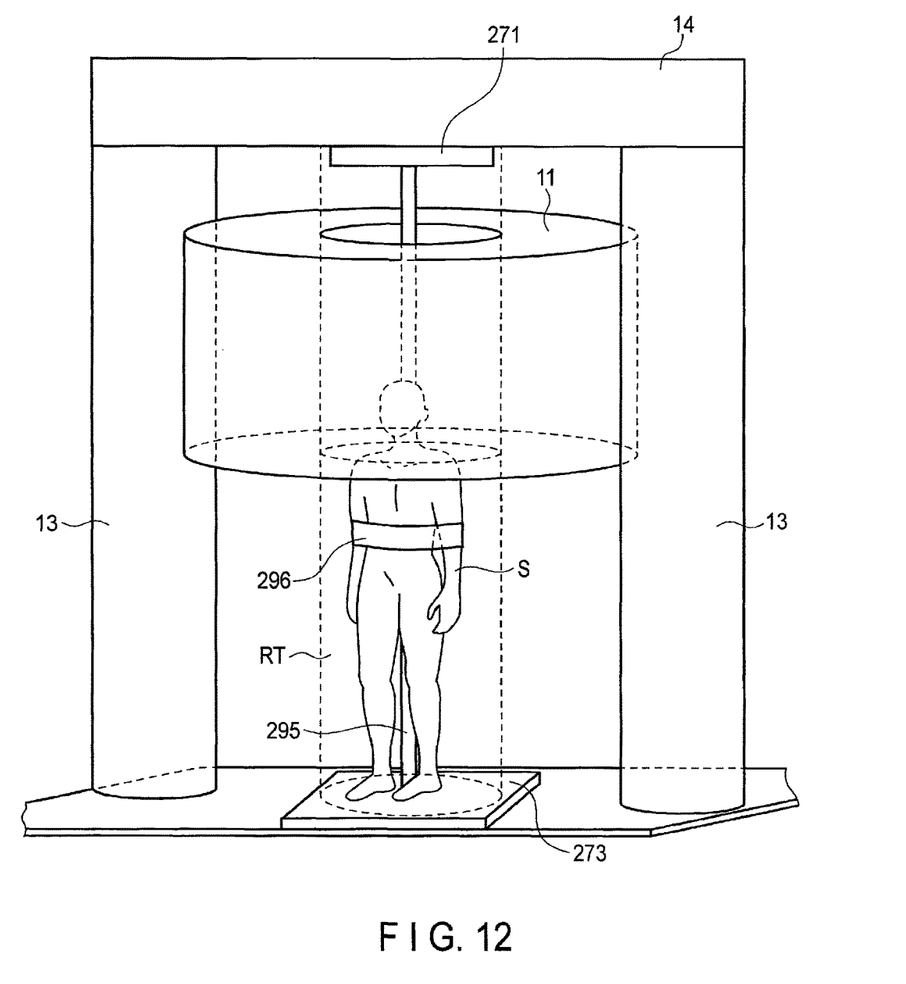
FIG. 12 shows the subject holder of FIG. 11 and a subject.

FIG. 11 shows one example of the subject holder 29 including one pillar 295. FIG. 12 shows the single-pillar subject holder 295 of FIG. 11 together with a subject S. As shown in FIGS. 11 and 12, the pillar 295 is fixed by the holder fixing equipment 27. Specifically, the upper end of the pillar 295 is fixed by the upper fixing part 271, and the lower end of the pillar 295 is fixed by the lower fixing part 273. The pillar 295 may be placed anywhere within the passage RT. For example, the upper fixing part 271 and the lower fixing part 273 fix the pillar 295 at the position where the pillar 295 can contact the back of the subject S as shown in FIGS. 11 and 12. By the subject S leaning its back on the pillar 295, the pillar 295 can maintain the subject S upright. Also, since the pillar 295 may be arranged so that the subject S may lean the depression along the center region of the back of the subject S, the pillar 295 can more easily hold the subject S as compared to the case of the two pillars 293.

In order to more reliably secure the subject S to the pillar 295, an accessory fastener 296, such as a band, may be detachably provided to the pillar 295 as shown in FIG. 12. With the accessory fastener 296, the subject S can be fastened to the pillar 295.

(Summary)

As described above, the X-ray computed tomography apparatus according to the embodiments includes the gantry body 11, and the holder fixing equipment 27. The gantry body 11 includes the bore 15 to include a field of view, and also includes the X-ray tube 17 and the X-ray detector 19 opposed to each other with the bore 15 therebetween. The gantry body 11 may be arranged so that the central axis of the bore 15 extends vertically. In this state, the holder fixing equipment 27 fixes the subject holder 29 in the passage RT of the bore 15 for retaining a subject within the passage RT.

Based on these configurations, the X-ray computed tomography apparatus according to one embodiment can lower the subject holder 29 from the upper fixing part 271. The lowered subject holder 29 can be fixed to the lower fixing part 273. Also, the X-ray computed tomography apparatus according to one embodiment can raise the subject holder 29 from the lower fixing part 273. The raised subject holder 29 can be fixed to the upper fixing part 271. Furthermore, the X-ray computed tomography apparatus according to one embodiment can fix the subject holder 29 by the lower fixing part 273. The subject is held by the subject holder 29 thus fixed according to these various modes, and the subject is fastened to the subject holder 29 using the accessory fastener 291, etc. so that X-ray CT can be performed for the subject in the standing position. Since the subject holder 29 extends through the bore 15, subjects (patients) are freed from unwanted body motions and their safety and sense of security can be ensured. Moreover, fixation of the subject holder 29 does not require a lot of time and effort. Added to these, no major floor construction is required, and therefore, the man-hours for installation can be reduced. With all of these advantages, X-ray computed tomography apparatuses capable of holding and imaging a standing subject at a given position can be achieved by the embodiments.

The term "processor" in the descriptions is intended to cover, for example, a dedicated or general-purpose processor, circuit (circuitry), processing circuit (circuitry), operation circuit (circuitry), arithmetic circuit (circuitry), or may include the following types of circuits: an application-specific integrated circuit (ASIC), a simple programmable logic device (SPLD), a complex programmable logic device (CPLD), a field programmable gate array (FPGA), or the like. In addition, each of the components (processors) of the embodiments is not limited to a single processor, but may be attained by a plurality of processors. Furthermore, multiple components (processors) may be attained by a single processor.

While certain embodiments have been described, they have been presented by way of example only, and are not intended to limit the scope of the inventions. Indeed, the novel embodiments described herein may be embodied in a variety of other forms. Furthermore, various omissions, substitutions and changes in the form of the embodiments may be made without departing from the spirit of the inventions. The accompanying claims and their equivalents are intended to cover such forms or modifications as would fall within the scope and spirit of the inventions.

The invention claimed is:

1. An X-ray computed tomography apparatus to scan a standing subject to obtain cross-sections of the subject along a central axis, the X-ray computed tomography apparatus comprising:
   a gantry body with a bore with both ends open to accommodate the standing subject to be examined, the gantry body comprising an X-ray tube and an X-ray detector so that the bore has a field of view;
   a pair of columns which support the gantry body so that the gantry body is vertically movable along the central axis of the bore extending vertically to a floor on which the X-ray computed tomography apparatus is installed; and
   a subject holder in a shape of a ladder or in a shape of at least one pillar for holding the standing subject to be examined, the subject holder having (1) a lower end removably fixed to a recess portion provided on the floor and directly below a passage of the bore and (2) an upper end, wherein the subject holder is fixed independently from a movement of the bore and is adapted so that, in an extended state where the subject holder extends through the bore of the gantry body, the upper end is connected to a beam bridging over the pair of columns and the lower end is connected to the recess portion.

2. The X-ray computed tomography apparatus according to claim 1, wherein, in a phase of attaching the subject to the subject holder, the pair of columns places the gantry body at an upper end of a movable range for scanning.

3. The X-ray computed tomography apparatus according to claim 2, wherein the recess portion provided on the floor fixes a longitudinal end of the subject holder vertically below the gantry body during imaging.

4. The X-ray computed tomography apparatus according to claim 1, wherein the recess portion provided on the floor fixes a longitudinal end of the subject holder vertically below the gantry body during imaging.

5. The X-ray computed tomography apparatus according to claim 1, wherein the recess portion provided on the floor fixes the subject holder so that the subject holder is inserted into and taken out from the bore.

6. The X-ray computed tomography apparatus according to claim 1, wherein the subject holder maintains an upright posture of the subject within the passage.

7. The X-ray computed tomography apparatus according to claim 6, wherein the subject holder is at least one pillar fixed to the floor by the recess portion provided on the floor during imaging.

8. The X-ray computed tomography apparatus according to claim 1, wherein the subject holder is non-metal.

9. The X-ray computed tomography apparatus according to claim 1, wherein the pair of columns supports the gantry body so that the gantry body is rotatable about a horizontal axis.

10. The X-ray computed tomography apparatus according to claim 9, wherein the subject holder is a ladder.

11. The X-ray computed tomography apparatus according to claim 1, wherein in a phase of attaching the subject to the subject holder, the pair of columns places the gantry body at an upper end of a mechanical movable range, and
    the recess portion provided on the floor fixes the subject holder so that the subject holder extends through the bore and is contained in the passage with the gantry body placed at the upper end during imaging.

12. The X-ray computed tomography apparatus according to claim 11, wherein the recess portion provided on the floor fixes a longitudinal end of the subject holder vertically below the gantry body during imaging.

13. The X-ray computed tomography apparatus according to claim 1, wherein the subject holder is a ladder.

14. The X-ray computed tomography apparatus according to claim 1, wherein the subject holder is two pillars.

* * * * *